United States Patent
Karri et al.

(10) Patent No.: US 12,138,361 B2
(45) Date of Patent: Nov. 12, 2024

(54) ACTIVATING EMITTING MODULES ON A WEARABLE DEVICE

(71) Applicant: International Business Machines Corporation, Armonk, NY (US)

(72) Inventors: Venkata Vara Prasad Karri, Visakhapatnam (IN); Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 755 days.

(21) Appl. No.: 17/353,954

(22) Filed: Jun. 22, 2021

(65) Prior Publication Data

US 2022/0401607 A1 Dec. 22, 2022

(51) Int. Cl.
| | |
|---|---|
| *G05B 23/02* | (2006.01) |
| *A61L 2/025* | (2006.01) |
| *A61L 2/08* | (2006.01) |
| *A61L 2/24* | (2006.01) |
| *G05B 19/042* | (2006.01) |
| *G06F 1/16* | (2006.01) |
| *G06F 17/16* | (2006.01) |

(52) U.S. Cl.
CPC ............... *A61L 2/24* (2013.01); *A61L 2/025* (2013.01); *A61L 2/085* (2013.01); *G06F 1/163* (2013.01); *A61L 2202/11* (2013.01); *A61L 2202/14* (2013.01); *A61L 2202/16* (2013.01)

(58) Field of Classification Search
CPC . A61L 2/24; A61L 2/025; A61L 2/085; A61L 2201/11; A61L 2201/14; A61L 2201/16; G06F 1/163

USPC .......................................................... 700/90
See application file for complete search history.

(56) References Cited

U.S. PATENT DOCUMENTS

| | | | |
|---|---|---|---|
| 9,775,520 B2* | 10/2017 | Tran | A61B 5/7264 |
| 10,048,835 B2* | 8/2018 | Cotier | G06F 9/452 |
| 10,268,888 B2* | 4/2019 | Osterhout | H04N 23/661 |
| 11,191,466 B1* | 12/2021 | Heneghan | A61B 5/01 |
| 2015/0127365 A1 | 5/2015 | Rizvi | |
| 2018/0027908 A1 | 2/2018 | Greenly | |

(Continued)

OTHER PUBLICATIONS

Authors et. al.: Disclosed Anonymously, "Mobile System & Method for Smart Phone Microorganism/Surface Detection & Disinfection", An IP.com Prior Art Database Technical Disclosure, IP.com No. IPCOM000261385D, IP.com Electronic Publication Date: Feb. 27, 2020, 8 pages.

(Continued)

*Primary Examiner* — Md Azad
(74) *Attorney, Agent, or Firm* — Kimberly Zillig

(57) ABSTRACT

A system for activating an emitting module is provided. A computer device identifies (i) environment data relating to an environment, and (ii) user data relating to a user located within the environment, wherein the user is wearing a wearable computing device. The computing device predicts that the user will interact with a surface in the environment based, at least in part, on the environment data and the user data. The computing device selects at least one emitting module from a plurality of emitting modules on the wearable device based, at least in part, on a predicted proximity of the at least one emitting module to the surface. The computing device prompts the user to activate the at least one emitting module.

19 Claims, 6 Drawing Sheets

(56) References Cited

U.S. PATENT DOCUMENTS

| | | | | |
|---|---|---|---|---|
| 2018/0189568 A1* | 7/2018 | Powderly | ............... | G06V 40/20 |
| 2019/0188471 A1* | 6/2019 | Osterhout | ............... | G06F 3/012 |
| 2021/0319894 A1* | 10/2021 | Sobol | ....................... | G06N 7/01 |
| 2021/0343182 A1* | 11/2021 | Lu | ........................... | G09B 19/24 |
| 2022/0361810 A1* | 11/2022 | Price | .................... | A61B 5/7405 |

OTHER PUBLICATIONS

Mell et al., "The NIST Definition of Cloud Computing", Recommendations of the National Institute of Standards and Technology, Special Publication 800-145, Sep. 2011, 7 pages.

Owen, Malcolm, "Muscle-sensing Apple Watch band could detect gestures more accurately", Apple Insider, downloaded from the internet on Jul. 20, 2020, 12 pages, <https://appleinsider.com/articles/20/06/02/muscle-sensing-apple-watch-band-could-detect-gestures-more-accurately>.

Weiss et al., "Smartwatch-based Activity Recognition: A Machine Learning Approach", 2016 IEEE-EMBS International Conference on Biomedical and Health Informatics (BHI), pp. 426-429.

* cited by examiner

ACTIVATING EMITTING MODULES ON A WEARABLE DEVICE

BACKGROUND OF THE INVENTION

The present invention relates generally to the field of wearable smart devices, and more particularly to the use of infrared wave and ultrasonic emitting modules executing on wearable smart devices.

Generally, ultrasound are sound waves with frequencies higher than the upper audible limit of human hearing. In general, ultrasonic devices are used to detect objects and measure distances. In general, electromagnetic radiation, commonly referred to as infrared light, is used in thermal efficiency analysis, environmental monitoring, and remote temperature sensing.

SUMMARY

Embodiments of the present invention provide a method, system, and program product.

A first embodiment encompasses a method. One or more processors identify (i) environment data relating to an environment, and (ii) user data relating to a user located within the environment, wherein the user is wearing a wearable computing device. One or more processors predict that the user will interact with a surface in the environment based, at least in part, on the environment data and the user data. One or more processors select at least one emitting module from a plurality of emitting modules on the wearable device based, at least in part, on a predicted proximity of the at least one emitting module to the surface. One or more processors prompt the user to activate the at least one emitting module.

A second embodiment encompasses a computer program product. The computer program product includes one or more computer-readable storage media and program instructions stored on the one or more computer-readable storage media. The program instructions include program instructions to identify (i) environment data relating to an environment, and (ii) user data relating to a user located within the environment, wherein the user is wearing a wearable computing device. The program instructions include program instructions to predict that the user will interact with a surface in the environment based, at least in part, on the environment data and the user data. The program instructions include program instructions to select at least one emitting module from a plurality of emitting modules on the wearable device based, at least in part, on a predicted proximity of the at least one emitting module to the surface. The program instructions include program instructions to prompt the user to activate the at least one emitting module.

A third embodiment encompasses a computer system. The computer system includes one or more computer processors, one or more computer-readable storage media, and program instructions stored on the computer-readable storage media for execution by at least one of the one or more processors. The program instructions include program instructions to identify (i) environment data relating to an environment, and (ii) user data relating to a user located within the environment, wherein the user is wearing a wearable computing device. The program instructions include program instructions to predict that the user will interact with a surface in the environment based, at least in part, on the environment data and the user data. The program instructions include program instructions to select at least one emitting module from a plurality of emitting modules on the wearable device based, at least in part, on a predicted proximity of the at least one emitting module to the surface. The program instructions include program instructions to prompt the user to activate the at least one emitting module.

DETAILED DESCRIPTION

Detailed embodiments of the present invention are disclosed herein with reference to the accompanying drawings. It is to be understood that the disclosed embodiments are merely illustrative of potential embodiments of the present invention and may take various forms. In addition, each of the examples given in connection with the various embodiments is intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Embodiments of the present invention recognize that in a modernized digital environment, technology can be utilized to provide users with wearable smart devices that include pluralities of sensors and pluralities of various emitting modules, such as ultrasonic and/or infrared emitting modules. Embodiments of the present invention provide for an improved experience for users by utilizing sensors to analyze and identify when a user is likely to interact with an object within an environment, and to identify and select an emitting module from a plurality of emitting modules based on that identification.

Embodiments of the present invention provide a technological improvement over known solutions for sensors and emitting modules executing on a wearable smart device. Embodiments of the present invention provide servers and systems that improve over conventional systems by providing a more computationally efficient artificial intelligence (AI) system that reduces the overall system load. Embodiments of the present invention recognize that the incorporation of artificial intelligence allows the system to analyze the environment in real time and allow for an efficient determining of an emitting module from a plurality of emitting modules, which again, reduces overall system load.

The present invention will now be described in detail with reference to the Figures.

Figure 1:
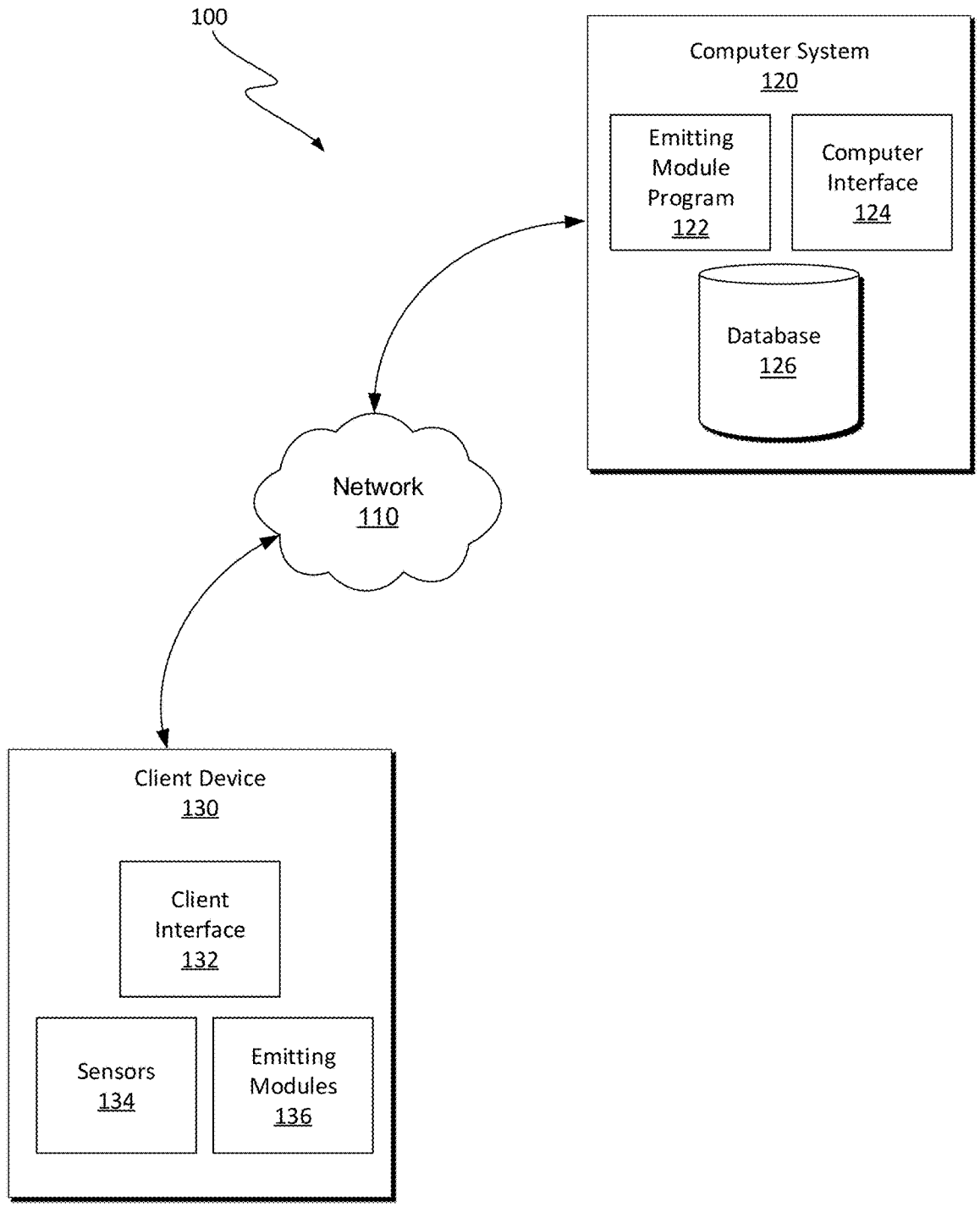
FIG. 1 is a functional block diagram illustrating a computing environment in which a system determines an emitting module for activation based, at least in part, on machine learning, in accordance with an exemplary embodiment of the present invention.

FIG. 1 is a functional block diagram illustrating a computing environment, generally designated 100, in accordance with an embodiment of the present invention. Computing environment 100 includes computer system 120 and Client device 130. Computer system 120 includes emitting module program 122, computer interface 124, and database 126. Client device 130 includes client interface 132, sensors 134, and emitting modules 136.

In various embodiments of the present invention, computer system 120 is a computing device that can be a standalone device, a server, a laptop computer, a tablet computer, a netbook computer, a personal computer (PC), a personal digital assistant (PDA), a smartwatch, a desktop computer or any programmable electronic device capable of executing machine readable program instructions and communications with client device 130. In another embodiment, computer system 120 represents a computing system utilizing clustered computers and components to act as a single pool of seamless resources. In general, computer system 120 can be any computing device or a combination of devices with access to client device 130 and network 110 and is capable of executing emitting module program 122, computer interface 124, and database 126. Computer system 120 may include internal and external hardware components as depicted and described in further detail with respect to FIG. 6.

In this exemplary embodiment, emitting module program 122 and computer interface 124 are stored on computer system 120. However, in other embodiments, emitting module program 122 and computer interface 124 may be stored externally and accessed through a communication network, such as network 110. Network 110 can be, for example, a local area network (LAN), a wide area network (WAN) such as the Internet, or a combination of the two, and may include wired, wireless or any other connection known in the art. In general, network 110 can be any combination of connections and protocols that will support communications between computer system 120 and client device 130, in accordance with a desired embodiment of the present invention.

Emitting module program 122 is depicted in FIG. 1 for illustrative simplicity. In various embodiments of the present invention, emitting module program 122 represents logical operations executing on computer system 120, where computer interface 124 manages the ability to view these logical operations and their results on computer system 120. Computer system 120 can include any number of logical operations that are managed and executed in accordance with emitting module program 122. In some embodiments, emitting module program 122 represents an administrator that analyzes input and output (I/O) data. Additionally, emitting module program 122, when executing an emitting module request, operates to monitor the I/O data that was analyzed and generates a modification based on, but not limited to, the analyzation operation. In some embodiments, emitting module program 122 determines whether a specific action is likely to take place and generates a modification request and communicates a notification to client device 130 indicating that a modification is required for client interface 132, sensors 134, and emitting modules 136 of client device 130.

Computer system 120 includes computer interface 124. Computer interface 124 provides an interface between computer system 120 and client device 130. In some embodiments, computer interface 124 can be a graphical user interface (GUI), a web user interface (WUI), or an image projector and can display text, documents, web browsers, windows, user options, application interfaces, instructions for operation, images, and holographic displays, and includes the information (such as graphic, text, and sound) that a program presents to a user and the control sequences the user employs to control the program. In some embodiments, computer system 120 accesses data communicated from client device 130 via a client-based application that runs on computer system 120. For example, computer system 120 includes mobile application software that provides an interface between computer system 120 and Client device 130.

Sensors 134 are depicted in FIG. 1 for illustrative simplicity. In various embodiments of the present invention, sensors 134 execute on client device 130, where sensors 134 communicate data to emitting module program 122. In various embodiments, sensors 134 represent computing devices that monitor and determine the surroundings of client devices 130 to identify objects within the environment. Additionally, in various embodiments, sensors 134 determine the environment of client device 130 in order to generate an emitting module request for inanimate objects and surfaces. In various embodiments, sensors 134 further include, but are not limited to, augmented reality eyewear or a headset that communicates with sensors 134 executing on client device 130 and computer system 120 over network 110. In various embodiments, sensors 134 determine whether specific action is likely to take place and generate data that is communicated to emitting module program 122, wherein emitting module program 122 generates an emitting module request and communicates the emitting module request to client device 130. Additionally, various other sensors 134 are present in FIG. 1, in which client device 130 utilize one or more sensors 134 to monitor user data and communicate user data to emitting module program 122 to generate an emitting module request. In various embodiments of the present invention, sensors 134 include various sensors within client device 130, including, but not limited to, (i) one or more proximity sensors which can be used to identify persons and objects, and (ii) sensors that monitor the various muscle movements of the user.

In various embodiments of the present invention, client device 130 represents any programmable electronic device capable of executing machine readable program instructions and communicating with computer system 120. In some embodiments, client device 130 represents a smartwatch and monitors muscle movements to identify patient data and communicate the user data to emitting module program 122. In some embodiments, client device 130 represents decontamination device that is capable of identifying that users will use or touch an object and decontaminate the object.

In various embodiments, emitting module program 122 communicates with database 126 and accesses user data regarding the user's muscle movement, environment data, and data regarding when the emitting module request should be initiated. Additionally, in various embodiments, emitting module program 122 communicates with database 126 and accesses data regarding when the emitting module request should not be initiated (e.g., surfaces that should not be subject to ultrasonic and/or infrared emissions).

In various embodiments of the present invention, emitting module program 122 receives I/O data in the form of (i.e., is included as a part of) user data and environment data. Emitting module program 122 analyzes the data and prepares a digital modification for client device 130. In various embodiments, emitting module program 122 communicates data that represents the emitting module request with program instructions instructing client device 130 to activate at least one emitting module in accordance with the (i) alert to user and (ii) user approval.

In various embodiments, emitting module program 122 receives a task to be completed from a user, where the task to be completed is associated with the surface that the user is likely to interact with. In various embodiments, emitting modules 136 represent a plurality of emitting modules electrically connected to the wearable computing device on the user. Various embodiments of the present invention provide that each respective emitting module of emitting modules 136 have their own respective purpose to complete a task. In various embodiments, at least one emitting module 136 is selected to complete the task associated with the surface requested by the user. In one example embodiment, a first emitting module 136 represents an LED and that the task to complete received from the user associated with the predicted surface within the environment is that the first emitting module 136 is to illuminate the predefined area within the environment that the user is located within. The first emitting module 136 is activated to illuminate the predefined location within the environment that the user is within. In a second example embodiment, a second emitting module 136 represents an infrared light capable of decontaminating a surface before a user interacts with the surface. In this second example embodiment, the task to completed received from the user is to decontaminate an elevator button before the user is predicted to interact with the elevator button (e.g., the surface). The second emitting module 136 is activated and decontaminates the elevator button prior to the user interacting with the elevator button.

In various embodiments of the present invention, emitting module program 122 continuously monitors data received from sensors 134 executing on client device 130. In various embodiments, emitting module program 122 monitors at various time periods the positioning of client device 130 and user data received from sensors 134. In various embodiments, emitting module program 122 determines that an emitting module request should be generated and communicates the request to a user of client device 130, where the emitting module request includes (i) an alert prompt instructing the user to select 'YES' or 'NO' and (ii) a set of program instructions instructing client device 130 to activate the at least one emitting module. Additionally, emitting module program 122 communicates a set of program instructions instructing the user how to properly utilize the selected emitting module before use (e.g., how to utilize the emitting module to decontaminate a surface). In various embodiments, the program instructions instructing client device 130 include, but are not limited to, instructions activate the emitting module (e.g., activate infrared light or ultrasonic sound waves), and instructions to align the emitting module to be pointed in a correct angle and direction within a threshold. Embodiments of the present invention provide that the emitting modules could be axially aligned on client device 130, where the emitting modules are capable of rotating within a threshold portion of a three-hundred and sixty degree (360) spherical axis. In various embodiments, program instructions to the user include, but are not limited to, an alert instructing the user to reply 'YES' or 'NO' about activating one or more of the emitting modules, instructions on how to orient and position the emitting modules to properly perform a desired task, such as decontaminating the object or surface, instructions relating to how long the user should orient and position the emitting modules over the object or surface, and a response box where the user can indicate to emitting module program 122 why the user chose to not activate the emitting modules.

In various embodiments, emitting module program 122 analyzes the response from the user relating to why the user chose to not initiate the emitting module request. In various embodiments, emitting module program 122 determines from the response from the user why in subsequent uses the emitting module request should not be generated. In one example embodiment, if emitting module program 122 generates an emitting module request and communicates it to the client device 130 and the user of client device 130 and the user respond 'NO' with an additional response indicating that the surface identified in the emitting module request is a second individual's hand before a handshake, then emitting module program 122 learns that this is an object that an emitting module request should not be generated for in subsequent uses. In an alternative embodiment, sensors 134 include, but are not limited to, an augmented reality eyewear or headset that analyzes the environment of the user and can identify objects and people. In this alternative embodiment, emitting module program 122 generates an emitting module request with program instructions and communicates the request to client device 130 and the user. The user responds 'NO' and further responds that the surface identified in the emitting module request in a second individual's hand before a handshake, and emitting module program 122 correlates this response with environment data from the augmented reality eyewear or headset and learns how to identify that a second individual is present in the environment, that a handshake will likely occur between the user and the second individual, and that emitting module program 122 should not initiate the emitting module request.

In various embodiments, client device 130 includes, but is not limited to, emitting modules 136 that execute on client device 130 to decontaminate objects in accordance with the emitting module request generated by emitting module program 122. In various embodiments, emitting modules 136 include, but are not limited to, an infrared radiation light, where the infrared radiation light operates to decontaminate an object without directly applying other general cleaning methods known in the art (e.g., soap and water). In various embodiments, infrared radiation technology allows for short cycle time, low energy consumption, no cycle residuals, and no toxicologic or environmental effects. In various embodiments, emitting modules 136 include, but are not limited to, an ultrasonic sound wave emitter, wherein the ultrasonic soundwave emitter operates to decontaminate an object through cavitation. Embodiments of the present invention provide that ultrasonic cavitation is an efficient, safe, and fast method of decontamination, where ultrasonic cavitation reduces time and eliminates microorganisms present on the objects. Embodiments of the present invention further provide that the ultrasonic soundwave emitter emits a frequency between 28 and 38 kHz to eliminate microorganisms present on the objects by breaking the microorganisms cell wall. Embodiments of the present invention further recognize that emitting modules 136 may include a wide variety of other emitting modules for completion of a wide variety of other tasks, including emitting modules and tasks known in the art as well as emitting modules and tasks to be developed in the future. In various embodiments, emitting modules 136 complete activities related to the surface within the environment that includes, but is not limited to, decontaminating the surface within the environment and illuminating the predefined location. In one example embodiment, emitting modules 136 include a light emitting diode (LED). In this example embodiment, emitting modules 136 include LEDs that involve applying a voltage to a semiconductor material, wherein the electrons are 'knocked loose' of the semiconductor material, in turn emitting particles of light energy, also known as photons. The LEDs can be utilized as a light source on the wearable smart device to allow the user to illuminate an area.

In various embodiments, client device 130 will include sensors 134 operating to emit an array of ultrasonic soundwaves or infrared wave light. In various embodiments, sensors 134 further operate to collect data to communicate to emitting module program 122. In various embodiments, emitting module program 122 identifies objects that the user is likely to interact with based on: (i) muscle movements of the user (e.g., user data) or (ii) identification of the user's environment through the use of an internet of things (IoT) system (e.g., environment data). In various embodiments, sensors 134 include, but are not limited to, a surface electromyography (EMG) that tracks the user's muscle movement based on recording the electrical potential connected to muscular fibers' depolarization (i.e., muscle contraction). In various embodiments, sensors 134 collect data that represents that the user is stretching out their hand and lifting their arm to either: (i) pickup an object or (ii) generally touch an object with their hand. Additionally, in various embodiments, client device 130 includes sensors 134 that identify environment data. In various embodiments, the environment data is obtained from sensors 134 including, but not limited to, (i) an IoT system within a predefined area and/or location (i.e., an office space, a home, etc.) that user frequents, works within, lives within, and (ii) an augmented reality eyewear or headset that is connected to client device 130 through a wireless connection known in the art. In various embodiments, the augmented reality eyewear or headset and the IoT system capture environment data with the user within the environment. In various embodiments, the augmented reality eyewear or headset analyzes the environment in which the user's line of sight is facing towards and further, augmented reality eyewear or headset identifies inanimate objects or surfaces within the user's line of sight. In various embodiments, emitting module program 122 receives this environmental data from the augmented reality eyewear or headset and determines whether to initiate the activation process. In various embodiments, sensors 134 communicate user data and environmental data to emitting module program 122.

In various embodiments, emitting module program 122 includes a machine learning model, where emitting module program 122 learns using historical training data. In various embodiments, the historical training data includes, but is not limited to, (i) user data that relates to a user picking up and/or touching an object, (ii) environment data that relates to a user wearing client device 130 within an IoT system, (iii) environment data that relates to a user wearing an augmented reality eyewear or headset and the augmented reality eyewear or headset identifying objects within the user's line of sight.

In various embodiments, emitting module program 122 analyzes the (i) user data and (ii) environment data and predicts if the user will be touching and/or picking up an object. In various embodiments, emitting module program 122 generates an emitting module request to decontaminate the object based on, at least, the prediction model. In various embodiments, as discussed above, emitting module program 122 generates the emitting module request to decontaminate the object, where emitting module program 122 communicates the emitting module request to the client device 130 with (i) program instructions instructing emitting modules 136 on how to decontaminate the object and (ii) program instructions coaching the user to respond to the alert prompt.

Embodiments of the present invention provide that sensors 134 and emitting modules 136 can be installed on (or disposed adjacent to) a wrist strap of a smartwatch. In various embodiments, the position and direction of sensors 134 and emitting modules 136 can be changed utilizing a pivot joint or other design known in the art. In various embodiments, emitting modules 136 can be properly aligned and/or projected towards the object to be decontaminated based at least in part, on the pivot joint or other design known in the art. In various embodiments, client device 130 operates within an IoT system (i.e., an office space, user's home, etc.), where the IoT system monitors the use of client device 130 and tracks the user's movement within the IoT system. In various embodiments, the IoT system identifies when the user will pick up and/or touch an object (e.g., buttons within an elevator, a community fridge, a community drinking fountain, etc.) and communicates this data to emitting module program 122 executing on computer system 120. In various embodiments, emitting module program 122 receives environment data from the IoT system that includes data indicating that the user will pick up and/or touch an object within the IoT system. In various embodiments, in response to receiving the environment data from the IoT system, emitting module program 122 generates an emitting module request with program instructions and communicates the emitting module request to client device 130. In various embodiments, emitting module program 122 tracks the user's movement within the IoT system and records the time when the emitting module request is generated, and further emitting module program 122 stores the data relating to the time and where the user was located in the IoT system when the emitting module request was generated on database 126.

Figure 2:
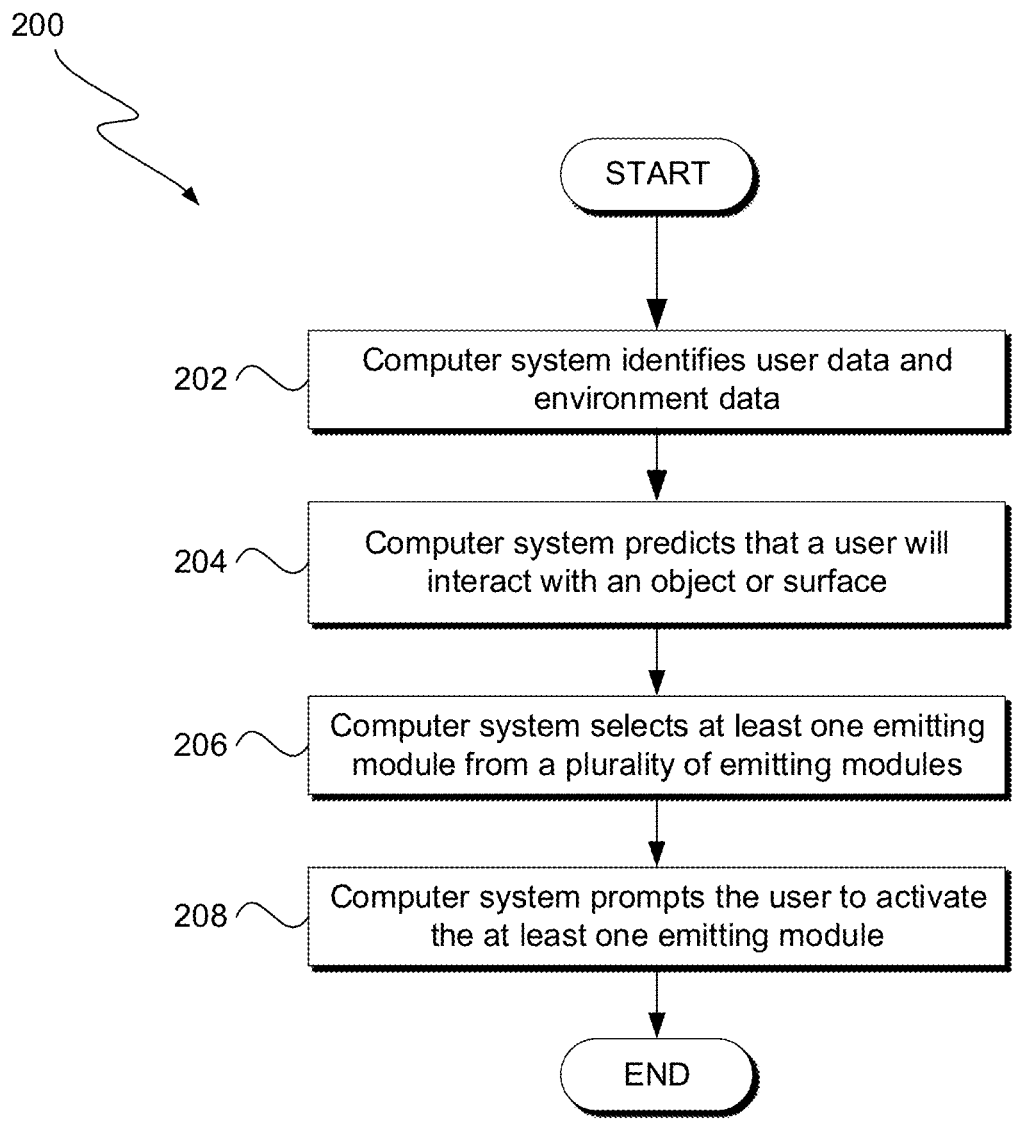
FIG. 2 is a flowchart which illustrates operational processes of executing a system to select at least one emitting module from a plurality of emitting modules, on a computing device within the environment of FIG. 1, in accordance with an exemplary embodiment of the present invention.

FIG. 2 is a flowchart depicting operations for an emitting module request within computing environment 100, in accordance with an illustrative embodiment of the present invention. More specifically, FIG. 2, depicts combined overall operations 200, of emitting module program 122. In some embodiments, operations 200 represent logical operations of emitting module program 122, wherein emitting module program 122 represents interactions between logical computing devices communicating with computer system 120 and various other computing devices connected to network 110. It should be appreciated that FIG. 2 provides an illustration of one implementation and does not imply any limitations with regard to the environments in which different embodiments may be implemented. Many modifications to the depicted environment may be made. In one embodiment, the series of operations, in flowchart 200, can be terminated at any operation. In addition to the features previously mentioned, any operations of flowchart 200, can be resumed at any time.

In operation 202, emitting module program 122 identifies user data and environment data. In various embodiments, emitting module program 122 receives user data and environment data from sensors 134, an augmented reality headset or eyewear, and/or an IoT system. In various embodiments, the user data and environmental data includes data pertaining to (i) the user's arm and hand movement, (ii) the user's movement within a defined area that IoT system is executing within (e.g., an office, user's home, public area), and (iii) various objects within the user's proximity (e.g., public elevator, community drinking fountain, community fridge, community garbage can).

In operation 204, emitting module program 122 predicts that a user will interact with an object or surface. In various embodiments, in response to emitting module program 122 identifying the user data and environment data, emitting module program 122 predicts whether the user will pick up and/or touch the object based on, at least, the trained machine learning model. In various embodiments, emitting module program 122 predicts that the user will pick up and/or touch an object, where emitting module program 122 correlates the current user data and environment data with historical training data. In various embodiments, emitting module program 122 predicts at a threshold level of certainty that the user will interact with an object.

In various embodiments, emitting module program 122 analyzes the received user data and environment data. In various embodiments, emitting module program 122 identifies whether (i) the user data relates to a user extending their hand to pick up and/or touch an object and (ii) environment data relates to a user moving towards an object that the user might pick up and/or touch. In various embodiments, emitting module program 122 includes a trained machine learning model that is trained to identify when a user will come into contact with an object where emitting modules 136 should be activated before the user touches and/or picks up the object. In various embodiments, emitting module program 122 is trained utilizing data that is related to a user picking up and/or touching an object that requires emitting modules 136 to be activated before use (i.e., buttons on a public elevator, community fridge in an office, community drinking fountain in a public space etc.).

In operation 206, emitting module program 122 selects at least one emitting module from a plurality of emitting modules. In response to emitting module program 122 predicting that the user will interact with an object, emitting module program 122 initiates the process of activating one or more emitting modules and generates an emitting module request. In various embodiments, emitting module program 122 generates the emitting module request that includes, but is not limited to, (i) program instructions instructing emitting modules 136 to activate from a plurality of emitting modules and (ii) an alert prompt with program instructions sent to client interface 132 to display the alert prompt to the user and coach the user to review the alert prompt and reply with 'YES' or 'NO'.

In operation 208, emitting module program 122 prompts the user to activate the at least one emitting module. In various embodiments, the alert prompt displayed to the user includes a textbox to provide the user the ability to respond why the user selected 'NO'. In various embodiments, the user responds with 'YES' and emitting module program 122 determines that the user wishes to proceed with activating at least one emitting module from a plurality of emitting modules—for example, to decontaminate the object. In various embodiments, emitting module program 122 communicates a set of program instructions instructing emitting modules 136 executing on client device 130 to decontaminate the object utilizing the at least one emitting module. In various embodiments, the user's response to the alert is communicated to emitting module program 122. In various embodiments, emitting module program 122 analyzes the user's response and identifies whether the user selected 'YES' or 'NO'. In various embodiments, if the user responded 'YES', then emitting module program 122 proceeds with the emitting module request and communicates program instructions instructing emitting modules 136 to decontaminate the identified object. In various embodiments, emitting module program 122 identifies that the user responded with 'NO' and further identifies the reasoning based on, at least, the user's response in the text box. In various embodiments, emitting module program 122 learns from the user's response to not complete the emitting module request based on, at least, (i) the user data, (ii) the environment data, and (iii) the user's response in the text box. In various embodiments, emitting module program 122 learns that similar emitting modules requests should not be completed in subsequent emitting module requests based, at least in part, on the user's 'NO' response. In various embodiments, emitting module program 122 actively monitors user responses and learns from the data.

In one example embodiment, emitting module program 122 predicts that a user will press a button on a public elevator to move to a different floor. In this embodiment, emitting module program 122 received user data and environment data, where emitting module program 122 identified based on, at least, environment data that the user was walking towards the elevator and further that the user entered the elevator. Additionally, emitting module program 122 received user data from sensors 134 executing on client device 130 that indicated that the user would extend their hand outward. In this embodiment, emitting module program 122 predicts that based on, at least, the received (i) user data and (i) environment data that the user will press a button on the public elevator. In this embodiment, emitting module program 122 generates a emitting module request that includes, but is not limited to, (i) program instructions instructing sensors 134 to activate a first emitting module to decontaminate the buttons and surface of the elevator control panel that emitting module program 122 predicted the user will interact with, and (ii) an alert with program instructions sent to client interface 132 to display the alert to the user and instruct the user to review the alert and reply with 'YES' or 'NO' to completing the emitting module request. In this embodiment, the alert is displayed to the user by client interface 132 executing on client device 130, where the user is prompted to respond 'YES' or 'NO' to decontaminating the buttons and elevator control panel before the user interacts with the elevator control panel. In this embodiment, the user responds with 'YES' and the response is communicated to emitting module program 122, where emitting module program 122 further communicates a set of program instructions instructing sensors 134 to decontaminate the elevator buttons and control panel utilizing infrared light to eliminate microorganisms before the user interacts with the elevator buttons and control panel. In this embodiment, emitting module program 122 communicates a set of program instructions coaching the user to raise their arm and wrist so that the faces of the infrared light sensors are in front of and/or are positioned over the elevator buttons and control panel. Additionally, emitting module program 122 coaches the user to hold their arm and wrist in the position to decontaminate the elevator buttons and control panel for a threshold period of time to eliminate the microorganisms. Upon the threshold period of time being reached, the infrared light sensor turns off and emitting module program 122 communicates a final alert notifying the user that the emitting module request has been completed and that the user may now interact with the elevator buttons and control panel.

In a second example embodiment, emitting module program 122 predicts that a user will extend their arm to open a public door using the door handle. In this embodiment, emitting module program 122 received user data and environment data, where emitting module program 122 identified that based on, at least, environment data obtained from an augmented reality eyewear or headset that the user was walking towards a public door. Additionally, emitting module program 122 received user data from sensors 134 executing on client device 130 that indicated that the user would extend their hand outward. In this embodiment, emitting module program 122 predicts based on, at least, the received (i) user data and (i) environment data that the user will interact with a public door handle and open the door. In this embodiment, emitting module program 122 generates a emitting module request that includes, but is not limited to, (i) program instructions instructing emitting modules 136 to decontaminate the door handle that emitting module program 122 predicted the user will interact with, and (ii) an alert with program instructions sent to client interface 132 to display the alert to the user and coach the user to review the alert and reply with 'YES' or 'NO' about completing the emitting module request. In this embodiment, the alert is displayed to the user by client interface 132 executing on client device 130, where the user is prompted to respond 'YES' or 'NO' to decontaminating the door handle before the user interacts with the door handle. In this embodiment, the user responds with 'NO and the response is communicated to emitting module program 122. Additionally, the user responds in the text box that the user intended to greet a person by extending their hand to interact with the person by shaking their hand. In this embodiment, emitting module program 122 communicates a set of program instructions instructing emitting modules 136 executing on client device 130 not to perform the emitting module request. Additionally, emitting module program 122 generates a set of program instructions informing the user that the emitting module request has been cancelled based on, at least, the user's response. In this embodiment, emitting module program 122 analyzes the user's response and learns from, at least, the user's response that the emitting module request should not be initiated in the subsequent emitting modules requests. Additionally, emitting module program 122 further learns that the environment data communicated from the augmented reality eyewear or headset was not a door within the view of the user, instead was a person that the user was walking towards and that the door handle was the other person's extended hand to perform a handshake. Emitting module program 122 stores this data on database 126 for subsequent predictions in the future.

In a third example embodiment emitting module program 122 predicts that predicts that a user has entered a dimly lit and/or unlit area. In this embodiment, emitting module program 122 received user data and environment data, where emitting module program 122 identified that based on, at least, environment data obtained from an augmented reality eyewear or headset that the user was walking into a dimly lit or unlit area. Additionally, emitting module program 122 received user data from sensors 134 (e.g., light sensors) executing on client device 130 that indicated that the area is dimly lit or unlit. In this embodiment, emitting module program 122 predicts based on, at least, the received (i) user data and (i) environment data that the area is dimly lit or unlit that the user is entering. In this embodiment, emitting module program 122 generates an emitting module request that includes, but is not limited to, (i) program instructions instructing emitting modules 136 to activate the LEDs operating on client device 130. Additionally, emitting module program 122 generates an alert with program instructions sent to client interface 132 to display the alert to the user and coach the user to review the alert and reply with 'YES' or 'NO' about completing the emitting module request. In this embodiment, the alert is displayed to the user by client interface 132 executing on client device 130, where the user is prompted to respond 'YES' or 'NO' to activating the LEDs to illuminate the area. In various embodiments, the user responds 'YES' to the alert and emitting module program 122 instructs the user to position their arm with the wearable computing device in front of their field of vision and above their head to fully illuminate the area (e.g., predefined location).

Figure 3:
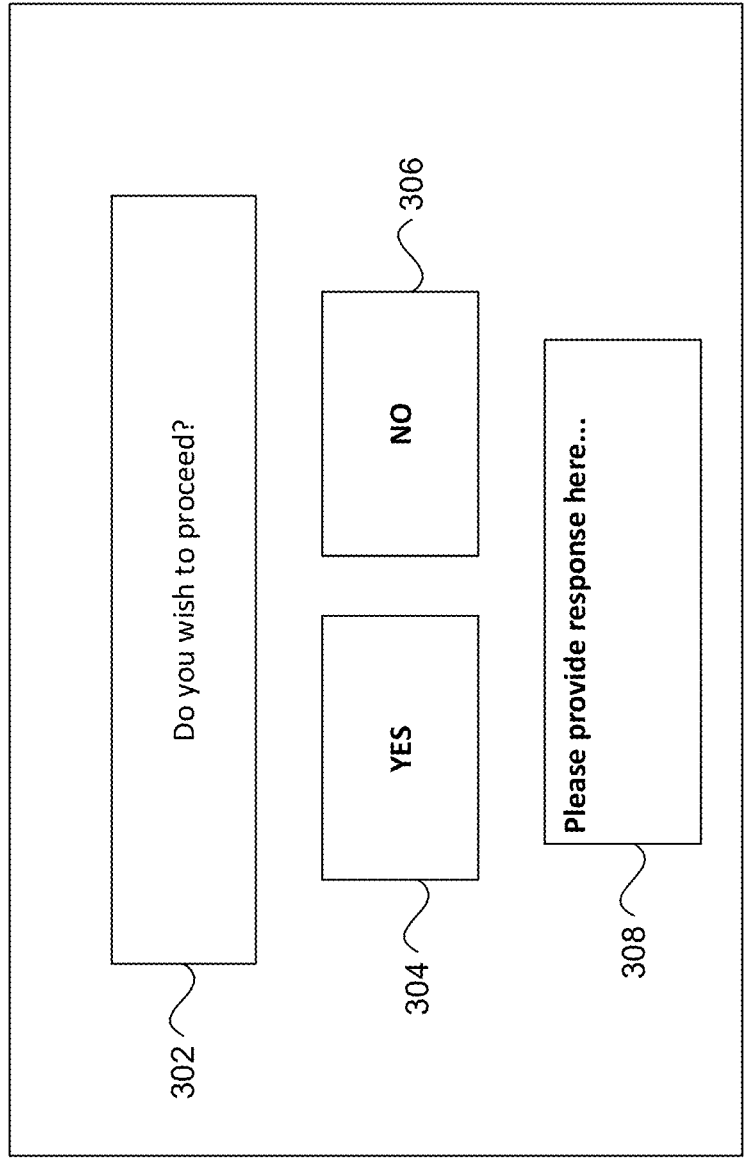
FIG. 3 depicts a screenshot view of a user preference screen, according to at least one embodiment of the present invention.

FIG. 3 depicts screenshot view 300. In various embodiments, block diagram represents an alert prompt displayed to a user by client interface 132 executing on client device 130, where the alert prompt was communicated by emitting module program 122. In various embodiments, the alert prompt includes, but is not limited to, (i) a prompt 302 inquiring whether the user wishes to proceed with the emitting module request (ii), response options 304 and 306 (a) 'YES' and (b) 'NO', respectively, and (iii) a text box 308 that allows the user to elaborate why the user chose to not complete the emitting module request. In various embodiments, the user selects either 'YES' or 'NO'. Additionally, in various embodiments, if the user selects 'NO' the user may include additional text in text box 308 that indicates why the user chose not to complete the emitting module request. In various embodiments, the user's response may include: (i) "Not opening a door, I am shaking a person's hand", (ii) "Not picking up a public object, I am picking up my personal water bottle", and (iii) "I am not in a public space, I do not need to decontaminate the object or surface". In various embodiments, emitting module program 122 learns from, at least, (i) the user's responses, (ii) user data, and (iii) environment data received. In various embodiments, emitting module program 122 further learns when to generate the emitting module request based on (i) user data and (ii) environment data received and correlates this received data with data and models stored on database 126.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
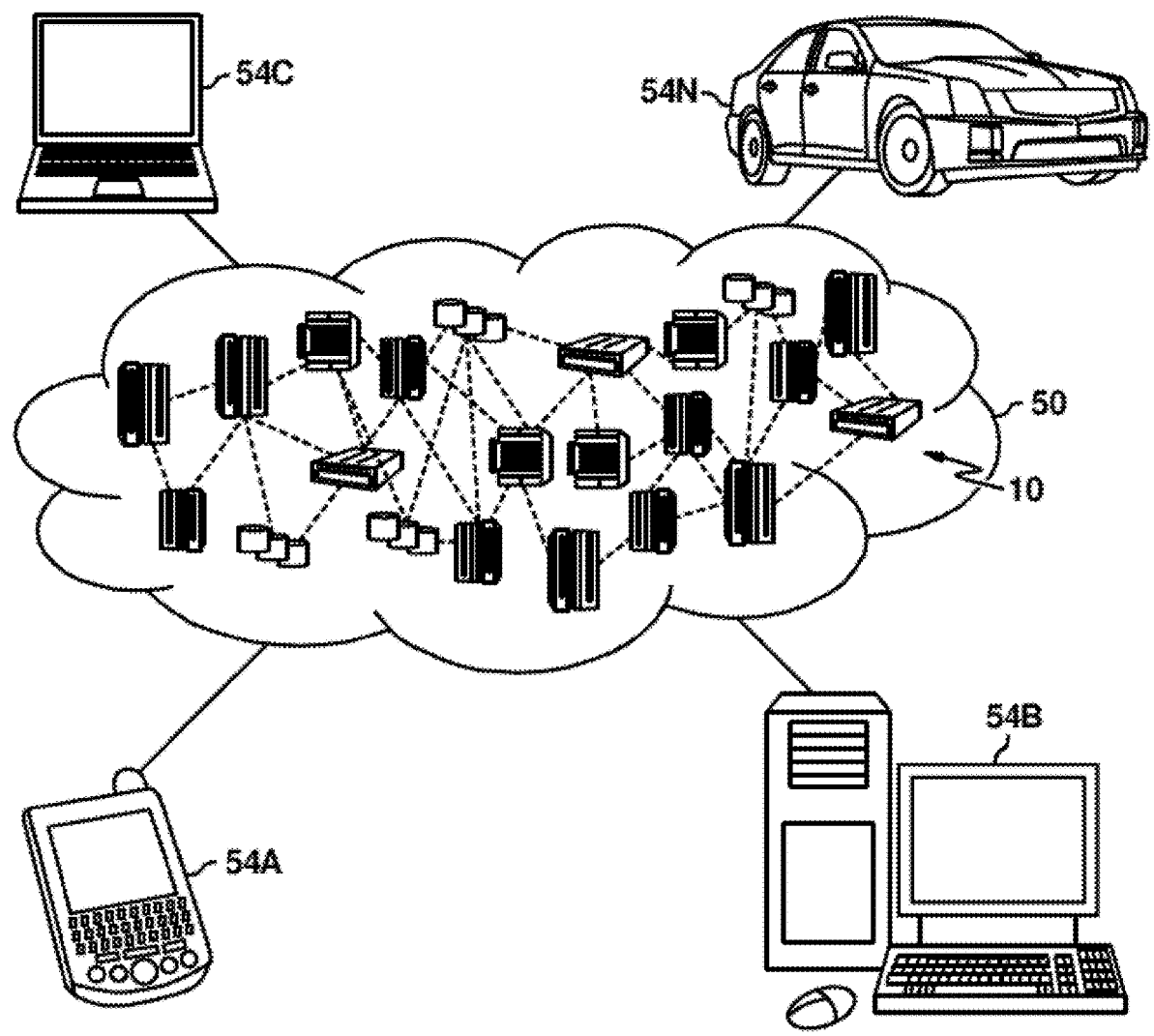
FIG. 4 depicts a cloud computing environment, according to at least one embodiment of the present invention.

Referring now to FIG. 4, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
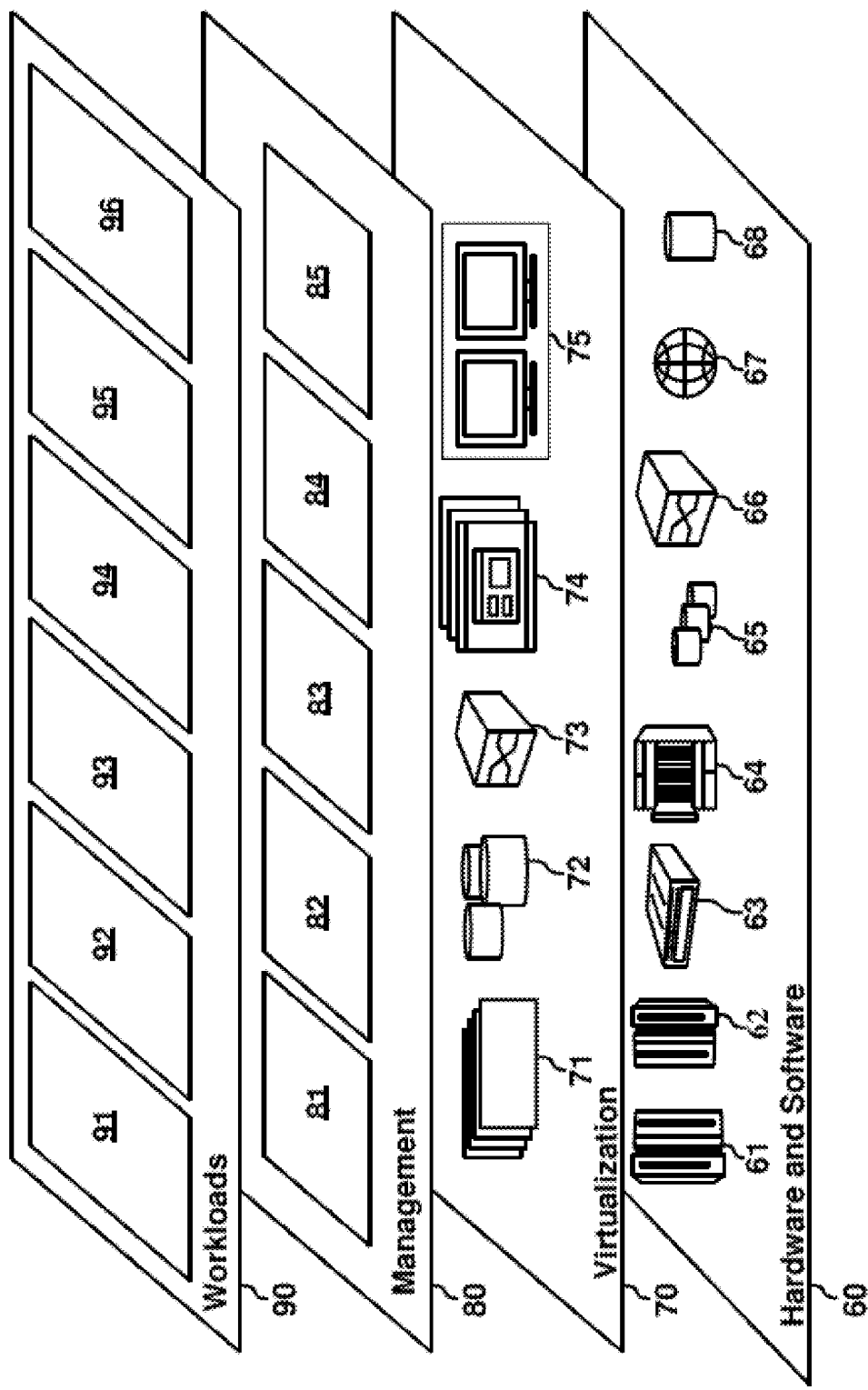
FIG. 5 depicts abstraction model layers, according to at least one embodiment of the present invention.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and providing soothing output 96.

Figure 6:
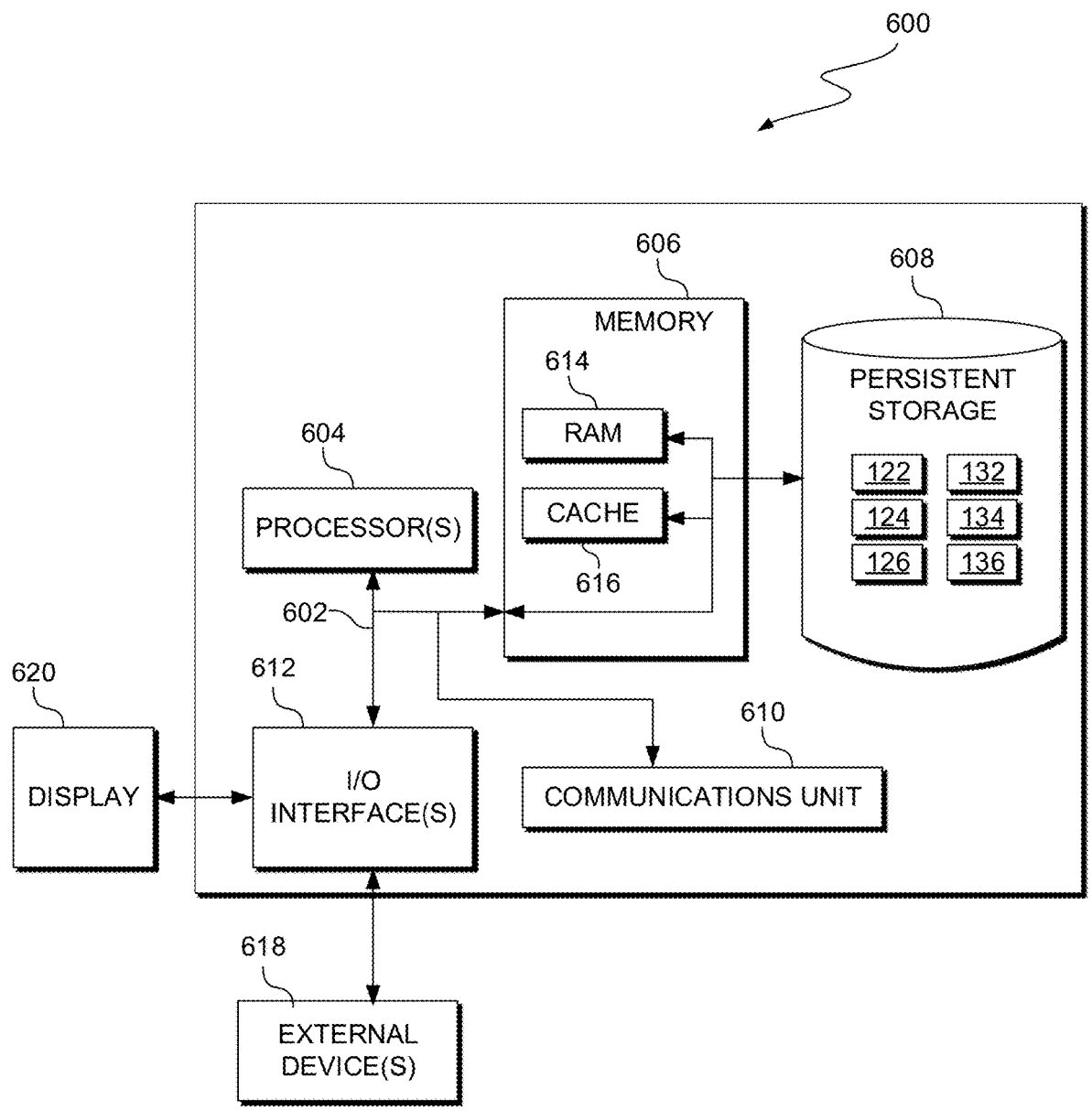
FIG. 6 depicts a block diagram of components of one or more computing devices within the computing environment depicted in FIG. 1, in accordance with an exemplary embodiment of the present invention.

FIG. 6 depicts a block diagram, 600, of components of computer system 120 and client device 130, in accordance with an illustrative embodiment of the present invention. It should be appreciated that FIG. 6 provides only an illustration of one implementation and does not imply any limitations with regard to the environments in which different embodiments may be implemented. Many modifications to the depicted environment may be made.

Computer system 120 and client device 130 includes communications fabric 602, which provides communications between computer processor(s) 604, memory 606, persistent storage 608, communications unit 610, and input/output (I/O) interface(s) 612. Communications fabric 602 can be implemented with any architecture designed for passing data and/or control information between processors (such as microprocessors, communications and network processors, etc.), system memory, peripheral devices, and any other hardware components within a system. For example, communications fabric 602 can be implemented with one or more buses.

Memory 606 and persistent storage 608 are computer-readable storage media. In this embodiment, memory 606 includes random access memory (RAM) 614 and cache memory 616. In general, memory 606 can include any suitable volatile or non-volatile computer-readable storage media.

Emitting module program 122, computer interface 124, database 126, client interface 132, sensors 134, and emitting modules 136 are stored in persistent storage 608 for execution and/or access by one or more of the respective computer processors 604 via one or more memories of memory 606. In this embodiment, persistent storage 608 includes a magnetic hard disk drive. Alternatively, or in addition to a magnetic hard disk drive, persistent storage 608 can include a solid state hard drive, a semiconductor storage device, read-only memory (ROM), erasable programmable read-only memory (EPROM), flash memory, or any other computer-readable storage media that is capable of storing program instructions or digital information.

The media used by persistent storage 608 may also be removable. For example, a removable hard drive may be used for persistent storage 608. Other examples include optical and magnetic disks, thumb drives, and smart cards that are inserted into a drive for transfer onto another computer-readable storage medium that is also part of persistent storage 608.

Communications unit 610, in these examples, provides for communications with other data processing systems or devices, including resources of network 110. In these examples, communications unit 610 includes one or more network interface cards. Communications unit 610 may provide communications through the use of either or both physical and wireless communications links. Emitting module program 122, computer interface 124, database 126, client interface 132, and sensors 134 may be downloaded to persistent storage 608 through communications unit 610.

I/O interface(s) 612 allows for input and output of data with other devices that may be connected to computer system 120 and client device 130. For example, I/O interface 612 may provide a connection to external devices 618 such as a keyboard, keypad, a touch screen, and/or some other suitable input device. External devices 618 can also include portable computer-readable storage media such as, for example, thumb drives, portable optical or magnetic disks, and memory cards. Software and data used to practice embodiments of the present invention, e.g., emitting module program 122, computer interface 124, database 126, client interface 132, sensors 134, and emitting modules 136, can be stored on such portable computer-readable storage media and can be loaded onto persistent storage 608 via I/O interface(s) 612. I/O interface(s) 612 also connect to a display 620.

Display 620 provides a mechanism to display data to a user and may be, for example, a computer monitor, or a television screen.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

It is to be noted that the term(s) such as, for example, "Smalltalk" and the like may be subject to trademark rights in various jurisdictions throughout the world and are used here only in reference to the products or services properly denominated by the marks to the extent that such trademark rights may exist.

What is claimed is:

1. A computer-implemented method, the method comprising:
    identifying, by one or more processors, (i) environment data relating to an environment, and (ii) user data relating to a user located within the environment, wherein the user is wearing a wearable computing device;
    predicting, by one or more processors, that the user will interact with a surface in the environment based, at least in part, on the environment data and the user data;
    selecting, by one or more processors, at least one emitting module from a plurality of emitting modules on the wearable computing device based, at least in part, on the predicting;
    prompting, by one or more processors, the user to activate the at least one emitting module;
    activating, by one or more processors, the at least one emitting module in response to an instruction from the user; and
    instructing, by one or more processors, the user to position the activated at least one emitting module within a proximity of the surface, wherein the at least one emitting module is adapted to decontaminate the surface.

2. The computer-implemented method of claim 1, wherein the predicting that the user will interact with the surface in the environment is further based, at least in part, on identifying: (i) that the user data relates to the user extending a hand to interact with the surface, and (ii) that the environment data relates to the user walking within a threshold proximity to the surface.

3. The computer-implemented method of claim 1, the method further comprising:
    determining, by one or more processors, a muscle movement of the user based, at least in part, on electrical potential data relating to muscular fiber depolarization received from sensors executing on the wearable computing device, wherein the user data includes the determined muscle movement of the user.

4. The computer-implemented method of claim 1, wherein:
the at least one emitting module is disposed adjacent to a wrist strap of the wearable computing device; and
the at least one emitting module includes a pivotal joint capable of aligning the at least one emitting module to project directly towards the surface.

5. The computer-implemented method of claim 1, wherein the predicting that the user will interact with the surface in the environment further includes correlating the user data and the environment data against historical user data and historical environment data that represent the user previously interacting with one or more surfaces within one or more environments.

6. The computer-implemented method of claim 1, the method further comprising:
receiving, by one or more processors, from the user, a task associated with the surface,
wherein the selecting the at least one emitting module from the plurality of emitting modules on the wearable computing device is further based, at least in part, on the task.

7. The computer-implemented method of claim 1, wherein the environment data is captured by an internet of things (IoT) system and an augmented reality headset.

8. A computer program product, the computer program product comprising:
one or more computer-readable storage media;
program instructions, stored on the one or more computer-readable storage media, to identify (i) environment data relating to an environment, and (ii) user data relating to a user located within the environment, wherein the user is wearing a wearable computing device;
program instructions, stored on at least one of the one or more storage media, to predict that the user will interact with a surface in the environment based, at least in part, on the environment data and the user data;
program instructions, stored on at least one of the one or more storage media, to select at least one emitting module from a plurality of emitting modules on the wearable device based, at least in part, on the predicting;
program instructions, stored on at least one of the one or more storage media, to prompt the user to activate the at least one emitting module;
program instructions, stored on at least one of the one or more storage media, to activate, by one or more processors, the at least one emitting module in response to an instruction from the user; and
program instructions, stored on at least one of the one or more storage media, to instruct, by one or more processors, the user to position the activated at least one emitting module within a proximity of the surface, wherein the at least one emitting module is adapted to decontaminate the surface.

9. The computer program product of claim 8, wherein the program instructions to predict that the user will interact with the surface in the environment are further based, at least in part, on identifying: (i) that the user data relates to the user extending a hand to interact with the surface, and (ii) that the environment data relates to the user walking within a threshold proximity to the surface.

10. The computer program product of claim 8, further comprising:
program instructions, stored on at least one of the one or more storage media, to determine a muscle movement of the user based, at least in part, on electrical potential data relating to muscular fiber depolarization received from sensors executing on the wearable computing device,
wherein the user data includes the determined muscle movement of the user.

11. The computer program product of claim 8, wherein:
the at least one emitting module is disposed adjacent to a wrist strap of the wearable computing device; and
the at least one emitting module includes a pivotal joint capable of aligning the at least one emitting module to project directly towards the surface.

12. The computer program product of claim 8, wherein the program instructions to predict that the user will interact with the surface in the environment include correlating the user data and the environment data against historical user data and historical environment data that represent the user previously interacting with one or more surfaces within one or more environments.

13. The computer program product of claim 8, further comprising:
program instructions, stored on at least one of the one or more storage media, to receive, from the user, a task associated with the surface,
wherein the program instructions to select the at least one emitting module from the plurality of emitting modules on the wearable computing device are further based, at least in part, on the task.

14. A computer system, the computer system comprising:
one or more processors, one or more computer-readable memories and one or more computer-readable storage media;
program instructions, stored on at least one of the one or more storage media for execution by at least one of the one or more processors via at least one of the one or more memories, to identify (i) environment data relating to an environment, and (ii) user data relating to a user located within the environment, wherein the user is wearing a wearable computing device;
program instructions, stored on at least one of the one or more storage media for execution by at least one of the one or more processors via at least one of the one or more memories, to predict that the user will interact with a surface in the environment based, at least in part, on the environment data and the user data;
program instructions, stored on at least one of the one or more storage media for execution by at least one of the one or more processors via at least one of the one or more memories, to select at least one emitting module from a plurality of emitting modules on the wearable device based, at least in part, on the predicting;
program instructions, stored on at least one of the one or more storage media for execution by at least one of the one or more processors via at least one of the one or more memories, to prompt the user to activate the at least one emitting module;
program instructions, stored on at least one of the one or more storage media for execution by at least one of the one or more processors via at least one of the one or more memories, to activate, by one or more processors, the at least one emitting module in response to an instruction from the user; and program instructions, stored on at least one of the one or more storage media for execution by at least one of the one or more processors via at least one of the one or more memories, to instruct, by one or more processors, the user to position the activated at least one emitting module within a proximity of the surface, wherein the at least one emitting module is adapted to decontaminate the surface.

15. The computer system of claim 14, wherein the program instructions to predict that the user will interact with the surface in the environment are further based, at least in part, on identifying: (i) that the user data relates to the user extending a hand to interact with the surface, and (ii) that the environment data relates to the user walking within a threshold proximity to the surface.

16. The computer system of claim 14, further comprising:
program instructions, stored on at least one or the one or more storage media for execution by at least one of the one or more processors via at least one of the one or more memories, to determine a muscle movement of the user based, at least in part, on electrical potential data relating to muscular fiber depolarization received from sensors executing on the wearable computing device,
wherein the user data includes the determined muscle movement of the user.

17. The computer system of claim 14, wherein:
the at least one emitting module is disposed adjacent to a wrist strap of the wearable computing device; and
the at least one emitting module includes a pivotal joint capable of aligning the at least one emitting module to project directly towards the surface.

18. The computer system of claim 14, wherein the program instructions to predict that the user will interact with the surface in the environment include correlating the user data and the environment data against historical user data and historical environment data that represent the user previously interacting with one or more surfaces within one or more environments.

19. The computer system of claim 14, further comprising:
program instructions, stored on at least one or the one or more storage media for execution by at least one of the one or more processors via at least one of the one or more memories, to receive, from the user, a task associated with the surface,
wherein the program instructions to select the at least one emitting module from the plurality of emitting modules on the wearable computing device are further based, at least in part, on the task.

* * * * *